US005984963A

United States Patent [19]
Ryan et al.

[11] Patent Number: 5,984,963
[45] Date of Patent: *Nov. 16, 1999

[54] ENDOVASCULAR STENTS

[75] Inventors: Carol A. Ryan, Lowell; Gary L. Boseck, Boxford; Michael F. Weiser, Groton; Samuel J. Santosuosso, Stoneham, all of Mass.; Stanley B. Levy, Wilmington, Del.; Gary L. Loomis, Morris Township, N.J.; George J. Ostapchenko; Mark E. Wagman, both of Wilmington, Del.

[73] Assignee: Medtronic AVE, Inc., Santa Rosa, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/636,783

[22] Filed: Apr. 23, 1996

Related U.S. Application Data

[63] Continuation of application No. 08/033,049, Mar. 18, 1993, abandoned.

[51] Int. Cl.$^6$ ...................................................... A61F 2/04
[52] U.S. Cl. .............................. 623/12; 623/1; 604/265; 606/198
[58] Field of Search ............................ 604/265; 606/102, 606/191, 192, 199, 195, 198, 151–156; 623/1, 11, 12, 901

[56] References Cited

U.S. PATENT DOCUMENTS

| | | |
|---|---|---|
| 3,502,069 | 3/1970 | Silverman . |
| 4,140,126 | 2/1979 | Choudhury . |
| 4,267,842 | 5/1981 | Archibald . |
| 4,312,920 | 1/1982 | Pierce ........................................ 623/1 |

(List continued on next page.)

FOREIGN PATENT DOCUMENTS

| | | |
|---|---|---|
| 0 361 912 | 4/1990 | European Pat. Off. . |
| 0382014 | 8/1990 | European Pat. Off. . |
| 0 441 516 | 8/1991 | European Pat. Off. . |
| 0621017 | 10/1994 | European Pat. Off. . |
| 3640745 | 6/1987 | Germany . |
| 661665 | 8/1987 | Switzerland . |
| WO 88/03752 | 11/1983 | WIPO . |

OTHER PUBLICATIONS

Watanuki et al., "Experimental Studies of a Non–Woven Vascular Prosthesis for Use in . . . ", World J. Surg., 2, 867–872, 1978.
Palmaz et al., "Expandable Intraluminal Graft: A Preliminary Study", Radiology, 156: 73–77 (1985).
Wright et al., "Percutaneous Endovascular Stents: An Experimental Evaluation", Radiology, 156: 69–72 (1985).
Palmaz et al., "Expandable Intraluminal Vascular Graft: A Feasibility Study", Surgery, 99: 199–204 (1986).
Wallace et al., "Tracheobronchial Tree: Expandable Metallic Stents Used in Experimental . . . ", Radiology 158: 309–312 (1986).
Palmaz et al., "Atherosclerotic Rabbit Aortas: Expandable Intraluminal Grafting", Radiology, 160: 723–726 (1986).
Charnsangavej et al., "Stenosis of the Vena Cava: Preliminary Assessment with Expandable . . . ", Radiology, 161: 295–298 (1986).

(List continued on next page.)

*Primary Examiner*—Wynn Wood Coggins
*Assistant Examiner*—A. T. Nguyen
*Attorney, Agent, or Firm*—Sterne, Kessler, Goldstein & Fox, P.L.L.C.

[57] ABSTRACT

Endovascular stents capable of being cut from a flat piece of material are described. The endovascular stents may be bioabsorbable, multilayered and may have structural configurations allowing them to maintain low profiles in vivo. Methods of manufacturing endovascular stents and methods of using endovascular stents are also described.

25 Claims, 13 Drawing Sheets

U.S. PATENT DOCUMENTS

| | | | |
|---|---|---|---|
| 4,321,711 | 3/1982 | Mano | 623/1 |
| 4,503,569 | 3/1985 | Dotter . | |
| 4,512,762 | 4/1985 | Spears . | |
| 4,553,545 | 11/1985 | Maass et al. . | |
| 4,560,374 | 12/1985 | Hammerslag . | |
| 4,580,568 | 4/1986 | Gianturco . | |
| 4,627,844 | 12/1986 | Schmitt . | |
| 4,641,653 | 2/1987 | Rockey . | |
| 4,649,922 | 3/1987 | Wiktor . | |
| 4,655,771 | 4/1987 | Wallsten . | |
| 4,660,560 | 4/1987 | Klein . | |
| 4,662,885 | 5/1987 | DiPisa, Jr. . | |
| 4,665,918 | 5/1987 | Garza et al. . | |
| 4,681,110 | 7/1987 | Wiktor . | |
| 4,705,517 | 11/1987 | DiPisa, Jr. . | |
| 4,732,152 | 3/1988 | Wallsten et al. . | |
| 4,733,665 | 3/1988 | Palmaz . | |
| 4,739,762 | 4/1988 | Palmaz . | |
| 4,740,207 | 4/1988 | Kreamer . | |
| 4,743,252 | 5/1988 | Martin | 623/1 |
| 4,762,128 | 8/1988 | Rosenbluth . | |
| 4,768,507 | 9/1988 | Fischell et al. . | |
| 4,770,664 | 9/1988 | Gogolewski . | |
| 4,776,337 | 10/1988 | Palmaz . | |
| 4,787,900 | 11/1988 | Yannas . | |
| 4,793,348 | 12/1988 | Palmaz . | |
| 4,795,458 | 1/1989 | Regan . | |
| 4,800,882 | 1/1989 | Gianturco . | |
| 4,834,747 | 5/1989 | Gogolewski . | |
| 4,848,343 | 7/1989 | Wallsten et al. . | |
| 4,850,999 | 7/1989 | Planck | 623/12 |
| 4,877,030 | 10/1989 | Beck et al. . | |
| 4,878,906 | 11/1989 | Lindemann et al. . | |
| 4,878,908 | 11/1989 | Martin . | |
| 4,886,062 | 12/1989 | Wiktor . | |
| 4,893,623 | 1/1990 | Rosenbluth . | |
| 4,902,289 | 2/1990 | Yannas | 623/1 |
| 4,907,336 | 3/1990 | Gianturco . | |
| 4,922,905 | 5/1990 | Strecker . | |
| 4,923,464 | 5/1990 | DiPisa, Jr. . | |
| 4,950,227 | 8/1990 | Savin et al. . | |
| 4,955,859 | 9/1990 | Zilber . | |
| 4,969,458 | 11/1990 | Wiktor . | |
| 5,007,926 | 4/1991 | Derbyshire . | |
| 5,028,597 | 7/1991 | Kodama | 623/1 |
| 5,047,050 | 9/1991 | Arpesani | 623/1 |
| 5,059,211 | 10/1991 | Stack et al. . | |
| 5,078,726 | 1/1992 | Kreamer . | |
| 5,084,065 | 1/1992 | Weldon et al | 623/12 |
| 5,089,006 | 2/1992 | Stiles . | |
| 5,100,429 | 3/1992 | Sinofsky et al. . | |
| 5,266,073 | 11/1993 | Wall | 623/1 |
| 5,282,860 | 2/1994 | Matsuno | 623/1 |
| 5,449,382 | 9/1995 | Dayton . | |

OTHER PUBLICATIONS

Rosch et al., "Experimental Intrahepatic Portcaval Anastomosis: Use of Expandable Gianturco Stents", Radiology, 162:481–485 (1987).

Sigwart et al., "Intravascular Stents to Prevent Occlusion and Restenosis After Transluminal Angioplasty", NEJM 316:701–706, 1987.

Schatz et al., "Balloon–Expandable Intracoronary Stents in the Adult Dog", Circulation, 76:450–457 (1987).

Roubin et al., "Early and Late Results of Intracoronary Arterial Stenting After Coronary . . . ", Circulation, 76:891–897 (1987).

Zollikofer et al., "Endovascular Stenting of Veins and Grafts: Preliminary Clinical Experience", Radiology, 167:707–712 (1988).

Barth et al., "Flexible Tantalum Stents Implanted in Aortas and Iliac Arteries: Effects in . . . ", Radiology, 175: 91–96 (1990).

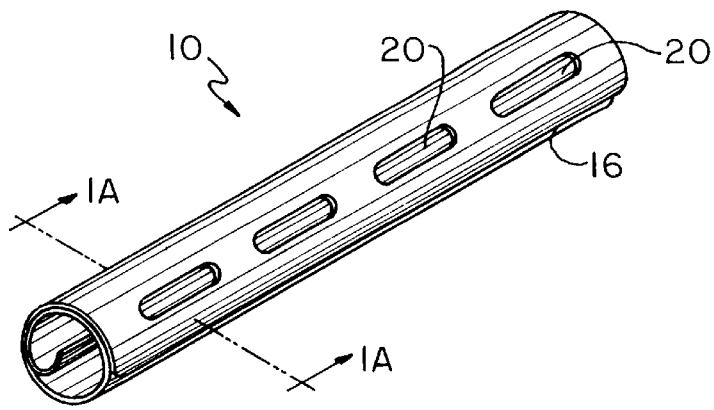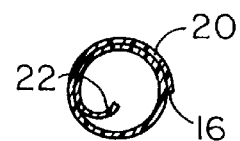
Fig.1  Fig.1A
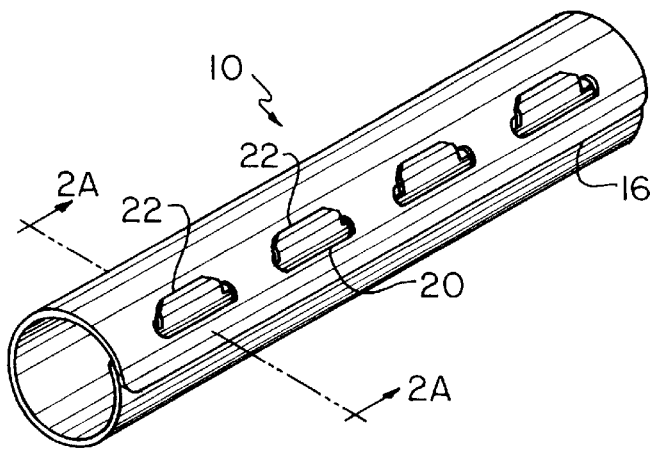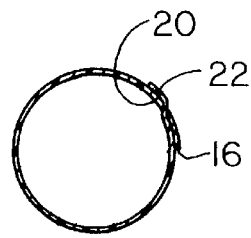
Fig.2  Fig.2A
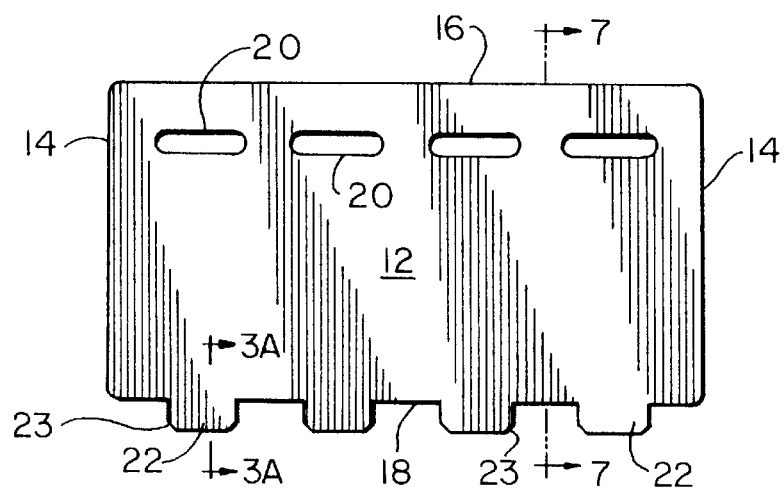
Fig.3

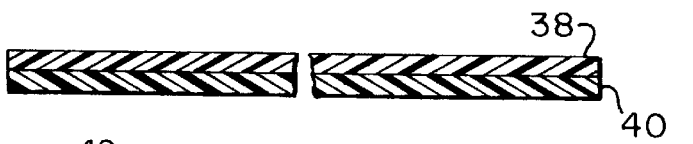
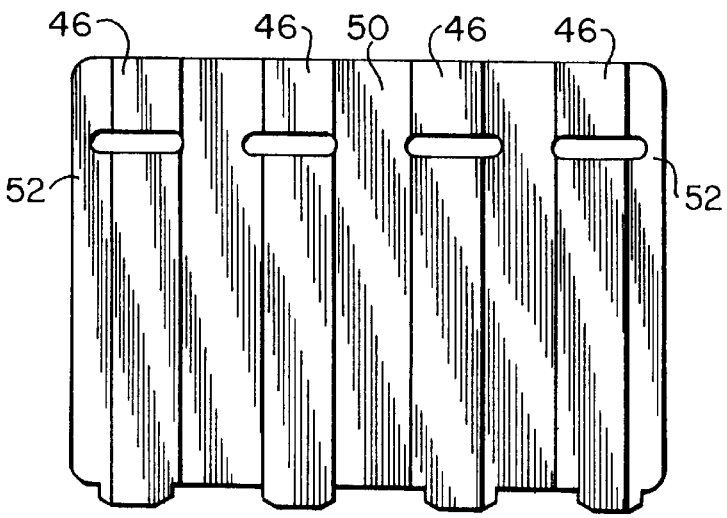
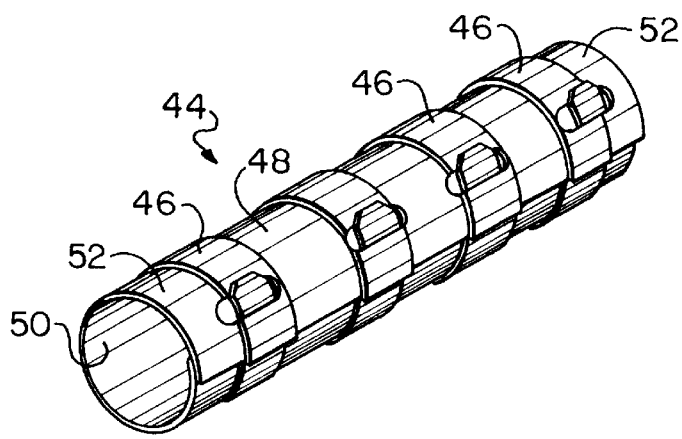

ENDOVASCULAR STENTS

This is a continuation, of application Ser. No. 08/033,049, filed Mar. 18, 1993, now abandoned.

FIELD OF THE INVENTION

This invention relates to endovascular stents adapted for percutaneous transluminal delivery to a selected site in a blood vessel.

BACKGROUND OF THE INVENTION

Balloon angioplasty is a medical procedure to widen obstructed blood vessels narrowed by plaque deposits. The procedure may be used in coronary or peripheral arteries. In an angioplasty procedure a catheter having a special inflatable balloon on its distal end is navigated through the patient's arteries and is advanced through the artery to be treated to position the balloon within the narrowed region (stenosis). The region of the stenosis is expanded by inflating the balloon under pressure to forcibly widen the artery. After the artery has been widened, the balloon is deflated and the catheter is removed from the patient.

A significant difficulty associated with balloon angioplasty is that in a significant number of cases the artery may again become obstructed in the same region where the balloon angioplasty had been performed. The repeat obstruction may be immediate (abrupt reclosure) which is usually caused by an intimal flap or a segment of plaque or plaque-laden tissue that loosens or breaks free as a result of the damage done to the arterial wall during the balloon angioplasty. Such abrupt reclosure may block the artery requiring emergency surgery which, if not performed immediately, may result in a myocardial infarction and, possibly, death. This risk also necessitates the presence of a surgical team ready to perform such emergency surgery when performing balloon angioplasty procedures. More commonly, a restenosis may occur at a later time, for example, two or more months after the angioplasty for reasons not fully understood and which may require repeat balloon angioplasty or bypass surgery. When such longer term restenosis occurs, it usually is more similar to the original stenosis, that is, it is in the form of cell proliferation and renewed plaque deposition in and on the arterial wall.

Various types of endovascular stents have been proposed and used as a means for preventing restenosis. The stents typically are tubular devices capable of maintaining the lumen of the artery open. The stent is placed inside the blood vessel after the angioplasty has been performed. A catheter typically is used to deliver the stent to the treated arterial region.

A number of patents have issued pertaining to various types of endovascular stents. Kreamer (U.S. Pat. No. 4,740,207 issued Apr. 26, 1988) discloses a radially expandable tubular stent having a latch mechanism by which a free longitudinal edge of the stent engages a longitudinally extending retaining ledge. The retaining ledge protrudes inwardly from the inner surface of the stent adjacent the opposite, free longitudinal edge of the stent. The stent has several disadvantages. First, the retaining ledge of the latching mechanism protrudes into the lumen of the stent, causing at least some obstruction to blood flow through the stent. Second, the bulk of the latching mechanism increases the profile (effective diameter) of the device when in the radially collapsed configuration. It is important for the collapsed stent to have a minimal collapsed profile allowing for easier advancement of the stent through tortuous or small diameter arteries. Third, that type of stent must be molded from a polymer in a procedure such as injection or compression molding, both of which have severe restrictions.

Such stents formed by injection molding may have wall thicknesses of the order of 0.010 inches to about 0.012 inches. Such wall thicknesses may occupy a significant portion of the lumen of the artery thereby causing potential difficulties in placement of the stent as well as potential reduction in the flow area through the artery. Additionally, such injection molded stents may require a reduction in the molecular weight of the polymer from which the stent is formed which may enhance the brittleness of the stent. Further, the injection molding process may cause warping or distortion of the stent.

U.S. Pat. Nos. 4,733,665; 4,739,762 and 4,776,337 to Palmaz disclose another type of expandable intraluminal vascular stent which, in an unexpanded configuration, can be mounted over the balloon on the distal end of a dilatation catheter. Expansion of the balloon causes a corresponding expansion of the stent. The stent is formed from metal and constructed to deform plastically and yieldably so that the stent will remain in its permanently deformed state after removal of the balloon.

European Patent Application 382,014 (Sigwart) discloses an intravascular stent in the form of a lattice-like member rolled into a small diameter spiral around the balloon of a catheter. It is retained in its small diameter configuration by a holding wire that is woven through the openings in the lattice and which can be pulled to release the rolled lattice so that it can be radially expanded by inflation of the balloon. One edge of the rolled-up lattice is provided with a plurality of outwardly projecting holding flaps that engage the lattice to prevent the device from collapsing after expansion.

U.S. Pat. No. 4,655,771 (Walsten) discloses a stent formed from a tubular braided mesh that is placed in the blood vessel in an elongated contracted configuration and self-expands when released to a larger diameter.

U.S. Pat. No. 4,649,922 (Wiktor) discloses a helical spring stent for implantation in an artery in which the stent is inserted in a contracted configuration. When released in the artery, the metallic stent springs open to its expanded larger diameter.

German Patent Application Publication No. 3640745 published Jun. 4, 1987 (Strecker) discloses a stent that can be locked in variable diameters in several successive steps.

Although many proposals have been made and considerable research is believed to have been undertaken to develop a satisfactory endovascular stent usable as an adjunct to angioplasty, no effective, satisfactory and generally accepted endovascular stent is believed to have been developed. Accordingly, there remains a need for such an effective device.

SUMMARY OF THE INVENTION

The present invention pertains to endovascular stents directed to various problems associated with prior art stents. The stents can be die cut from a flat sheet of material and do not have to be injection molded. The stents also have latching mechanisms that do not protrude significantly into the lumen of the stent and do not significantly increase the bulk of the stent. The stents may be made of bioabsorbable materials, alleviating concerns associated with stents being implanted in an individual over an indefinite amount of time. The bioabsorbable stents also may be made to have radiopaque characteristics allowing for fluoroscopic visualization or x-ray imaging in vivo.

The endovascular stent of the present invention may be formed from a multilayered sheet rolled in a spiral configuration, each layer selected for its physical properties and being adapted to perform one or more functions. The layers may be laminated together to form the composite sheet. The multiple layers allow for the production of a stent having a number of advantageous properties and/or functions. For example, the layers may be selected to have different surface properties at the inner and outer surfaces of the stent. One or more layers may carry releasable therapeutic drugs.

One embodiment of the stent of the present invention is in the form of a sheet rolled in a spiral configuration and having a latching mechanism which neither significantly protrudes into the lumen of the stent nor significantly increases the bulk of the stent. The latching mechanism secures the stent from collapsing after it has been expanded within the artery. The latching mechanism has at least one tab formed along a longitudinal edge of the sheet and adapted to extend through at least one slot formed adjacent the opposite edge of the sheet. The tabs extend through the slots when the stent is in its expanded position. The stent also may have multiple slots associated with each tab, the slots being located at different positions to enable the stent to be expanded selectively to and locked in one of a plurality of diameters. An advantage of the stent is that the tabs are coplanar with the sheet allowing it to be die cut in one place from a flat multilayered sheet as described above.

In a modified embodiment of the invention, the stent can be placed on the balloon of the delivery catheter in a "pre-locked" configuration. In the pre-locked device, the latching mechanism is engaged before the device is inserted into the artery, in its low profile (unexpanded) configuration, and remains engaged during and after expansion of the device. The pre-locked stent has further advantages in that it can be opened to various sizes depending on the extent of inflation of the balloon. The pre-locked stent may be in the form of a sheet rolled in a spiral configuration having at least one strip-like, elongated tab extending through a slot at all times, including when the stent is in a low profile, non-expanded state. The pre-locked stent can be stamped out of a flat sheet and does not require more complex molding procedures. It also can be made out of a multilayered sheet as described above. The latching mechanism of the pre-locked stent does not significantly increase the bulk of the stent or significantly protrude into the lumen of the stent.

In another aspect of the invention, the stent may be radiopaque to enable its visualization under fluoroscopy. The radiopaque stent incorporates a film defining radiopaque indicia that may be arranged to provide an indication of both the location and configuration of the stent when viewed fluoroscopically or when an x-ray image is made. The radiopaque indicia may be in the form of two spaced parallel stripes. The physician can determine the location of the stent fluoroscopically by viewing the stripes and can determine the configuration of the stent by determining whether the stripes are in registry with one another.

In another aspect of the invention, the stent is configured to have a high degree of longitudinal flexibility while maintaining substantial hoop strength. The longitudinal flexibility is desirable in order that the stent may conform more easily to the curves of tortuous arterial anatomy. A high hoop strength is necessary in order to prevent the stent from collapsing under the influence of contracting forces developed by the arterial wall. In this aspect of the invention, the stent may take the form of a plurality of expandable hoops connected to and spaced longitudinally along a spine-like strip. The spine-like strip is easily bent longitudinally of the device while the hoops provide significant hoop strength. Additionally, by forming the stent from a sheet, it can be formed from oriented film in a manner to provide for increased hoop strength of the hoops.

The present invention also pertains to improved methods for manufacturing the above-described stents including, particularly, the method of laminating multiple layers of materials together to form a single sheet used to make the stent and a method of manufacturing stents by stamping or cutting the entire stent, including the latching mechanism, from a flat sheet.

It is among the general objects of the present invention to provide improved endovascular stents.

It is another object of the invention to provide a stent having a locking mechanism which does not protrude adversely into the lumen of the stent.

A further object of the invention is to provide a stent having a low profile allowing for ease of advancement through tortuous and small diameter blood vessels.

It is another object of the invention to provide a stent which is bioabsorbable.

Still another object of the invention is to provide a stent which is both bioabsorbable and fluoroscopically visible.

A further object of the invention is to provide stents having radiopaque indicia allowing for visualization of both the location and configuration of the stent within the patient.

An additional object of the invention is to provide a multilayered stent formed from laminated sheets.

It is another object of the invention to provide an endovascular stent having improved longitudinal flexibility yet enhanced hoop strength.

It is still another object of the invention to provide multilayered stents in which the several layers may be formed to serve several functions.

BRIEF DESCRIPTION OF THE DRAWINGS

The foregoing and other objects and advantages of the invention will be appreciated more fully from the following detailed description of the invention with reference to the accompanying drawings wherein:

FIG. 1 is an illustration of one embodiment of the stent in a rolled-up low profile relaxed configuration;

FIG. 1A is a sectional illustration of the stent as seen along the line 1A—1A of FIG. 1;

FIG. 2 is an illustration of the stent of FIG. 1 in an expanded locked configuration;

FIG. 2A is a sectional illustration of the stent as seen along the line 2A—2A of FIG. 2;

FIG. 3 is a plan view of a sheet from which the stent of FIGS. 1 and 2 may be formed;

FIG. 7 is a sectional illustration of a portion of a sheet formable into a stent as may be seen along the line 7—7 of FIG. 3 in which the sheet is formed in multiple layers;

FIG. 7A is an illustration similar to FIG. 7 but of a sheet having three layers;

FIG. 8 is a somewhat diagrammatic illustration of in plan of a sheet from which a sheet may be formed in which the sheet is provided with a plurality of strips of material having a relatively high strength, the strips extending in a direction substantially perpendicular to the axis about which the sheet will be rolled to the stent configuration;

FIG. 9 is an exaggerated illustration of the sheet as shown in FIG. 8 as rolled into a stent configuration and defining an arrangement of a plurality of integral alternating hoops having high hoop strengths;

FIG. 10 is a sectional illustration taken along the line similar to FIGS. 7 and 7A illustrating a multilaminar arrangement in which a thin film of radiopaque material is captured between the inner and outer layers;

DESCRIPTION OF THE ILLUSTRATIVE EMBODIMENTS

Figure 3B:
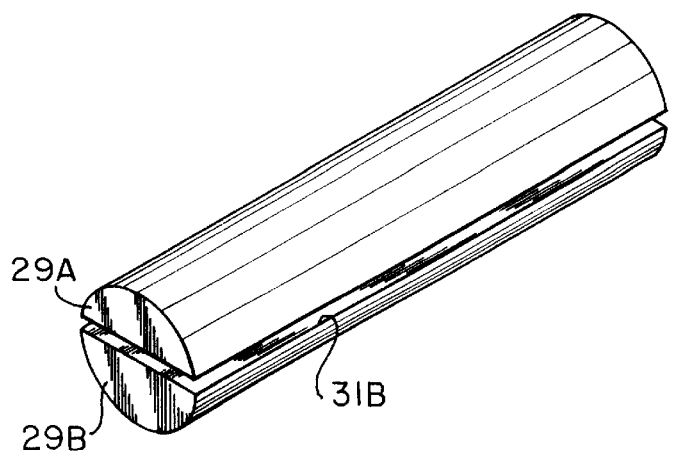
FIG. 3B is an illustration of the split mandrel used to roll the sheet into the stent configuration.
Figure 3A:
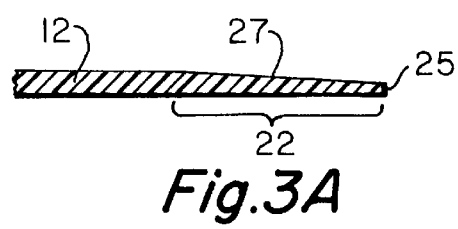
FIG. 3A is an enlarged sectional illustration of a locking tab as seen along the line 3A—3A of FIG. 3.
Figure 3C:
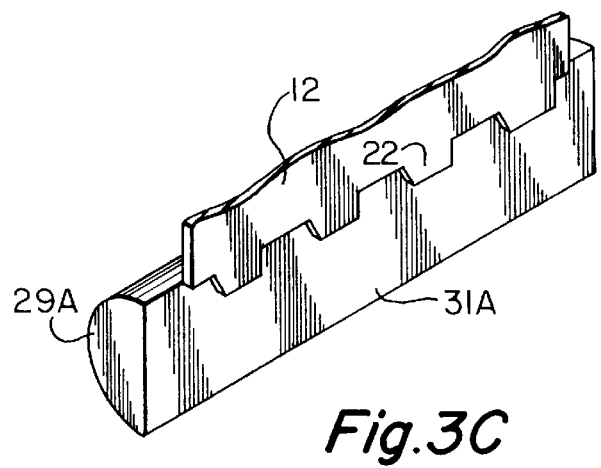
FIG. 3C is a diagrammatic illustration of the locking tabs of a sheet disposed against the flat surface of one-half of the split mandrel in readiness to be clamped by the other half of the split mandrel.
Figure 3D:
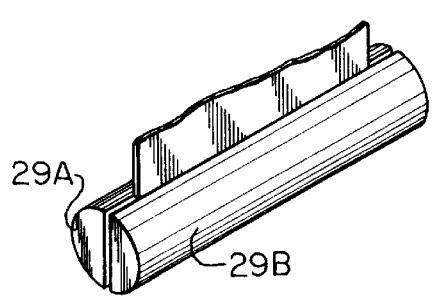
FIG. 3D is an illustration of both halves of the split mandrel with the tabs sheet captured therebetween and in readiness to roll the sheet about the mandrel.

FIGS. 1 and 2 illustrate, respectively, one embodiment of the stent in contracted (low profile) and expanded configurations, respectively. In its low profile configuration the stent is intended to be carried on the balloon portion of a balloon catheter, the balloon being deflated, also to present a low profile to facilitate navigation of the stent and balloon through a patient's arteries to the intended placement site. In accordance with the invention, the stent 10 may be formed from a sheet of suitable polymeric material, one embodiment of a pattern for the sheet being illustrated in FIG. 3. For the purpose of explanation, the sheet 12 may be considered as having a pair of side edges 14, an outer edge 16 and an inner edge 18. The edges 16, 18 are so designated to correspond to their relative location in the stent when the sheet 12 is rolled into the stent configuration. From FIGS. 1 and 2 it will be appreciated that the outer edge 16 will be disposed on the outside of the tubular stent while the inner edge 18 will be disposed interiorally of the stent. One or more tab-receptive slots 20 are formed in the sheet 12 along the outside edge 16. A corresponding number of tabs 22 are formed along the inside edge 18 in registry with their respective slots 20.

As will be described in further detail, it is preferred to form the tabs 22 so that when the sheet 12 is rolled into its low profile tubular configuration, the tabs will be straight, that is, flat and without any curl. This may be achieved, for example, by forming the tab to extend generally radially inwardly so that it does not become curled during the manufacturing process. It has been found that if the tabs are not formed flat but, instead, form a continuation of the curl of the stent, the ability of the tabs 22 to engage the slots 20 may be impaired. It is believed that such curl in the tab, although slight, tends to direct its leading edge away from the slot 20 so that it may not engage the slot effectively. Although the tab 22 extends radially inwardly when relaxed (see FIG. 1A), when mounted on and expanded by a balloon delivery catheter, the tab will flex outwardly and into locking engagement with the slot. The planar configuration of the tab 22 enhances substantially its ability to effectively engage the slot 20.

When expanded from the configuration in FIG. 1, the tubular stent will unroll and define a progressively increasing diameter until the tabs 22 pop into and through the slots 20 as suggested in FIG. 2. The expansion by the balloon then may stop, the balloon may be deflated to a low profile configuration and the balloon delivery catheter may be withdrawn, leaving the stent in place. The stent has some degree of resilience that tends to bias the expanded stent toward its contracted low profile configuration. That insures that the tabs 22 will be maintained in engagement with the slots 20, that engagement serving to prevent the stent from contracting to its low profile and effectively locking the device in its open, expanded configuration.

The sheet 12 preferably is formed from a bioabsorbable polymeric material such as a polylactide. The polymer should be formable into a sheet of desired thickness such that it can be readily die cut into the desired shape, such as indicated at FIG. 3. A preferred material is Poly-L-Lactide homopolymer. Alternately, it may be desirable to utilize a copolymer such as a 95/5 Poly-L, DL-Lactide to about 85/15 Poly-L, DL-Lactide. The copolymer may in some instances be advantageous because it has lower crystallinity and a lower melting point, is less brittle and is more easily processed.

By way of dimensional example, a polymeric sheet shown in FIG. 3 may have a length, measured from one side edge 14 to the other of about 15 mm and a width that may vary, depending on the diameter(s) to which the stent is intended to be expanded. Generally, in a representative example, the width of the sheet 12 may be between 7.5 to 11 millimeters for stents intended to have nominal expanded diameters of between about 2.0 to 3.0 mm. The slots 20 may be of the order of 1 mm wide and 3 mm long. The tab(s) 22 may be 1 mm long and 3 mm wide. The corners of the tab(s) 22 preferably are trimmed diagonally, as indicated at 23. The thickness of the polymeric sheet formed from which the sheet 12 is formed preferably is of the order of 0.002" to 0.004" for a stent to be used in smaller diameter blood vessels (e.g., coronary arteries) or of the order of 0.006" for larger (e.g., peripheral) blood vessels.

The process for making the stent includes forming a thin sheet of an appropriate polymeric material, for example, by extrusion or by solvent casting. Although compression molding from powdered polymeric also may be employed, that process does not lend itself readily to relatively low cost large scale manufacturing. The thickness of the polymeric sheet preferably is of the order of 0.002", it being desirable to maintain a low wall thickness, but without adversely affecting the hoop strength of the stent. The sheet then is die cut to the desired shape and size, such as, for example, the configuration illustrated in FIG. 3. The die cut sheet 12 then preferably is annealed in order to increase the crystallinity of the polymer. It is desirable that it be fully crystallized during the annealing process. A highly crystalline condition tends to result in a stent that will retain its strength and will display a slower rate of bioabsorbability than a less crystalline material. Typically, the annealing should take place above the glass transition temperature of the polymer and in an oven having a non-reactive atmosphere such as a vacuum oven or inert gas oven. By way of example, with the stent and material described above, the annealing may take place at a temperature of about 110° C. (for Poly-L-Lactide homopolymer) for about 15 minutes. Higher temperatures and longer oven times may be appropriate for copolymers. The annealed sheets then may be permitted to cool to room temperature.

The sheet or selected layers of the sheet may include a porous structure either by a mechanical process (e.g., laser etching) or by employing a material that is inherently porous. The porosities may be selected to optimize tissue ingrowth and endothelial coverage at the outer or inner surfaces of the stent. Different porosities may be selected for different portions of the stent, if desired.

After the annealing procedure has been completed, it may be desirable to trim the tabs 22 not only to include the trimmed corners 23 but also to taper the thickness of each tab. For example, the tab may be tapered in thickness as suggested in FIG. 3A to taper from the thickness of the main sheet (e.g, 0.002"–0.004") to of the order of 0.001" at the innermost edge 25 of the tab. The tapered configuration may be formed by skiving the tab, as with a sharp razor blade to form a skived surface 27 that makes an angle of the order of 20° with the opposed surface of the sheet 12 and tab 22. It has been found that by tapering the tab, the chance of the tab 22 failing to engage properly with its associated slot 20 is reduced.

With the sheet so formed and trimmed, it then may be rolled into the desired spiral configuration. Preferably, before rolling the sheet 12 onto a mandrel, the sheet is heated to above the glass transition temperature of the material (e.g., about 58° C. for Poly-L-Lactide) and is rolled onto the mandrel. It then is retained in the rolled configuration on the mandrel by slipping a polymeric tube such as a PTFE (Teflon®) over the rolled stent. The mandrel then may be removed. As described above, it is preferred that the tab(s) 22 be free of curls and, preferably, that the tabs extend radially inwardly of the stent in order to enhance the ability of the tab to engage the slot 20. In order to maintain the tabs 22 in their flat configuration, the sheet 12 may be rolled on a split mandrel illustrated in FIGS. 3B, 3C and 3D. As shown, the split mandrels 29A, 29B are placed on opposite sides of the tab 22 to grip the tab between the facing flat surfaces 31A, 31B and, in that configuration, the sheet 12 is rolled onto the mandrel. Pin vises may be used to secure the ends of the split mandrels together to clamp the tabs 22. The rolling may be done manually and preferably takes place while the sheet is maintained at about its glass transition temperature. After rolling, it is allowed to cool and the length of PTFE tubing (not shown) is slid over the rolled stent. The split mandrels 29A, 29B then may be removed, the PTFE tubing serving to hold the stent 10 in its rolled configuration. By way of example, the diameter of the half mandrels, together, may be of between about 0.040 to about 0.055" for stents having an intended nominal size of 2.0 to 4.0 mm expanded diameter. The PTFE tubing may have an inner diameter of the order of 0.073" to 0.093" for such range of stents. The PTFE tubes retain the stent in its intended low profile diameter.

It is desirable then to heat set the stents in their low profile configuration. In order to prevent the inwardly protruding tab(s) 22 from becoming deformed during the heat setting procedure, another set of mandrels (not shown) having generally D-shaped cross-sections may be provided. The D-shaped mandrels are adapted to fill the void within the rolled stent on opposite sides of the tab(s). The stent then is subjected to heat setting at a temperature above the glass transition temperature. For example, in the embodiment described using Poly-L-Lactide, the stent may be heat set at about 60° C. for about five minutes. Thereafter, the stent may be removed from the heat and may be allowed to cool to room temperature. The stent then may be loaded onto the delivery balloon catheter in readiness for delivery into the patient. It should be understood that when the stent is delivered to the intended placement site within the patient, it will be exposed to the patient's body temperature (of the order of 37° C.). As described below, the delivery balloon will be inflated to expand the stent and preferably will be maintained in an open configuration for a predetermined time interval. During the time that the stent is advanced into the patient and expanded by the balloon, it will rise to about body temperature. That will tend to soften the stent as it approaches the glass transition temperature of the material. Consequently, the stent will lose some of its ability to return fully to its heat set, contracted configuration although it should retain sufficient resilience to firmly engage the locking tabs, as described.

Figure 4:
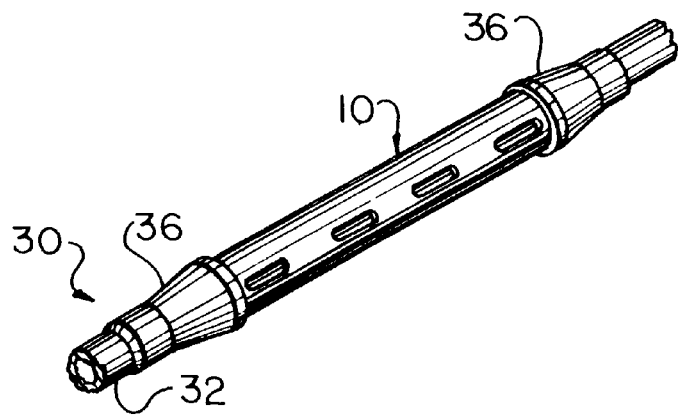
FIG. 4 illustrates a stent in accordance with the invention mounted on the balloon of a delivery catheter with the stent and balloon in a collapsed low profile configuration.
Figure 5:
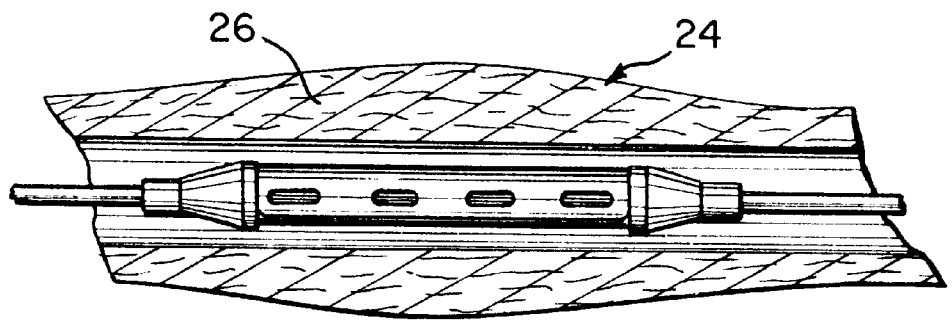
FIG. 5 is a diagrammatic illustration of the distal end of the catheter of FIG. 4 inserted into a portion of an artery after the artery has been dilated by an angioplasty procedure.
Figure 6:
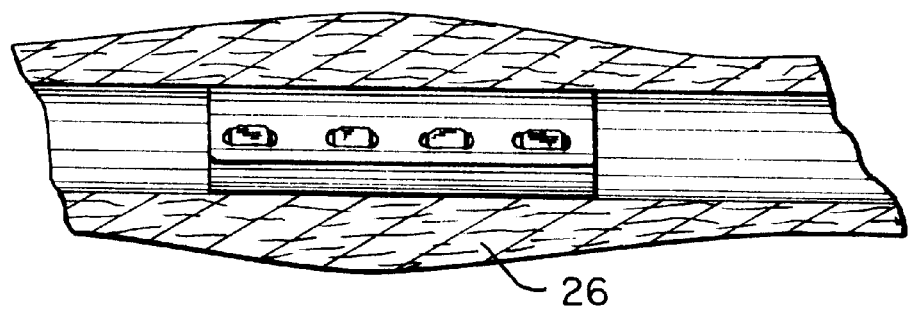
FIG. 6 is an illustration similar to FIG. 5 after the balloon has expanded the stent within the artery and after the catheter has been withdrawn.

FIGS. 4–6 illustrate, diagrammatically, the manner in which the stent may be placed in a portion of an artery in which an angioplasty has been performed. The artery 24 may have an appearance illustrated diagrammatically in FIGS. 5 and 6 in which the region where the stenosis existed before the angioplasty is characterized by a thickened portion 26 of the arterial wall, typically laden with proliferation of smooth muscle cells. FIG. 4 illustrates a stent 10 mounted on the balloon at the distal end of the delivery catheter 30. The catheter 30 includes a catheter shaft 32 and an attached balloon (disposed within the stent and not apparent in FIGS. 4–6) formed from a relatively inelastic material. We have found that Nylon 12 is a suitable material for the delivery balloon although other polymeric materials may be used as described in U.S. Pat. No. 5,108,416. The catheter preferably is provided with means by which the stent 10 can be engaged as by its ends to retain the stent 10 on the balloon while the device is navigated through the patient's arteries. The catheter may have any of a number of stent retaining devices such as, for example, flexible, yieldable end caps 36 mounted on the catheter shaft that engage the ends of the stent to hold the stent on the balloon during delivery but which release the ends of the stent when the balloon is expanded to expand the stent. Such catheters and stent retaining means are disclosed in U.S. Pat. No. 5,108,416 dated Apr. 28, 1992 to which reference is made and the disclosure of which is incorporated in its entirety as if fully set forth herein. FIG. 5 illustrates a device so placed before balloon and stent expansion. FIG. 6 illustrates the device after the balloon has expanded the stent into engagement with the inner surface of the lumen 28, and withdrawn from the artery, leaving the stent 10 in place.

Among the advantages of the invention is that by forming the stent from a flat polymeric sheet, it lends itself readily to multilayer, laminated construction in which the sheet is formed from two or more layers or films of different materials thereby to provide different characteristics as desired. For example, FIG. 7 illustrates, diagrammatically and in section, a portion of the sheet from which a stent may be made in which the sheet has a structural layer 38 formed from a suitable polymer (e.g., Poly-L-Lactide) and a specialized layer 40 laminated to the structural layer 38. The specialized layer, for example, may carry, releasably, a non-thrombogenic material (such as heparin) and is formed on the surface of the sheet 12 that will define the inner surface of the stent that is in direct contact with blood flow. Polymeric materials capable of carrying drugs, such as heparin, in a releasable form are well known to those skilled in the art. A stent so formed thus will expose the blood flowing through the artery to a non-thrombogenic surface, reducing the risk of platelet aggregation clotting. FIG. 7A illustrates, diagrammatically, a three-layer configuration for the sheet 12 similar to that of FIG. 7 but with an additional specialized layer 42 on the outer surface of the sheet. The specialized layer 42 may be impregnated with appropriate drugs adapted to retard further cellular proliferation within the arterial wall. For example, such drugs may include heparin.

FIGS. 8 and 9 illustrate, respectively, a sheet and a rolled-up stent formed from the sheet in which the stent 44 defines a plurality of hoops 46 spaced from each other along the length of the stent and connected by intermediate webs 48. The hoops 46 and webs 48 may be formed from the same or dissimilar materials. The strips that define the hoops 46 may be laminated to a base sheet 50 that defines the webs 48. The base sheet 50 is less rigid, either by material selection, relative thickness or both, as compared to the strips that define the webs 46. When rolled into the stent configuration as shown in FIG. 9, the hoops 46 will provide hoop strength for the stent to aid in resisting collapse under the constricting forces that may develop in the artery. The portions of the base sheet 50 that define the intermediate webs 48 are more flexible and enhance the longitudinal flexibility of the stent. Longitudinal flexibility is desirable in order that the stent can more easily navigate tortuous arteries during placement of the device. Additionally, the stent 44 may be formed so that the margins 52 will be formed from the more flexible base sheet 50. When rolled to the stent configuration, the resulting stent will have relatively soft, flexible end edges. The soft, flexible ends reduce risk of the stent digging into and possibly damaging the intimal lining of the artery. The soft flexible edge can also aid in alleviating some of the damage that might otherwise be caused at the interface between the vessel wall and the more rigid tubular stent due to compliance mismatch.

FIG. 10 illustrates, diagrammatically and in section, a section of sheet from which a stent may be formed in which a film 54 of radiopaque material is laminated between two layers 56, 58 of polymeric material. Inclusion of such a radiopaque film enables the stent to be viewed fluoroscopically or on X-ray images to determine its position in the patient.

If desired, the tensile properties of the sheet from which the stents are formed may be increased by orienting the film from which the sheets are cut. Techniques for orienting polymeric films are well known in the art. The film may be oriented biaxially or uniaxially. Unbalanced biaxial orientation is preferred, where the film is more oriented in the circumferential direction than in the longitudinal direction.

Figure 11B:
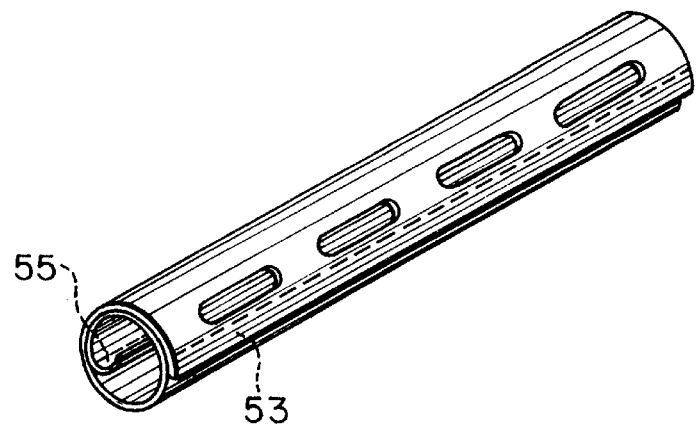
FIG. 11B is an illustration of the sheet of FIG. 11A rolled into a stent and in its low profile configuration.
Figure 11C:
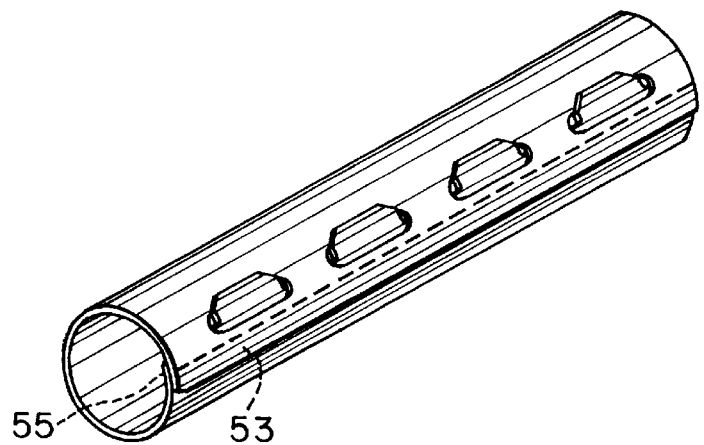
FIG. 11C is an illustration of the stent of FIG. 11B expanded and locked and illustrating the relative position of the radiopaque strips.
Figure 11A:
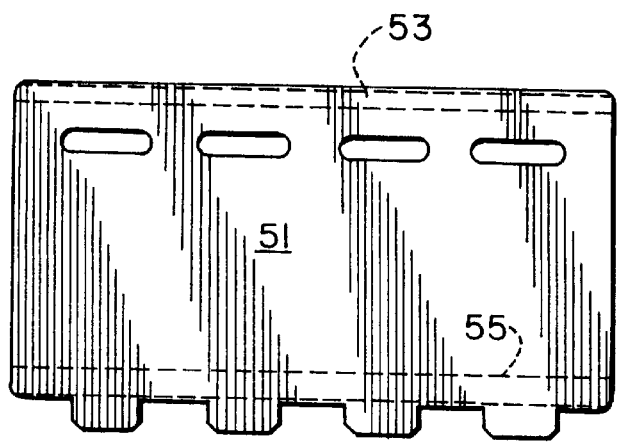
FIG. 11A is a plan view of a sheet from which a stent may be rolled in which the sheet is provided with a pair of strips of radiopaque material, the strips being parallel to the axis about which the stent will be rolled.

FIG. 11A illustrates diagrammatically a sheet 51 from which a stent may be formed which incorporates two stripes 53, 55 of radiopaque material. The stripes 53, 55, in this embodiment, extend lengthwise of the axis about which the stent will be rolled to its tubular configuration.

FIG. 11B illustrates a stent so formed in its low profile configuration. The radiopaque stripes 58 are located so that when in the low profile configuration, they will be spaced from each other but when the stent is expanded (FIG. 11C), the stripes 58 will be in registry with each other. Thus, the fluoroscopic or X-ray images presented by the stent when in the low profile configuration will be distinguishable from the image presented by the expanded configuration. In the low profile configuration (FIG. 11B), two distinct radiopaque lines may be observed. In the expanded configuration (FIG. 11C), the stripes 58 will be in registry thereby presenting a single, darker fluoroscopic image. Thus, not only the position but the open configuration of the stent may be determined by the physician.

The radiopaque stripes or other radiopaque indicia may be applied on the sheet by various techniques for applying metallic films to polymeric substrates. For example, the radiopaque indicia may be applied by low temperature arc vapor deposition (LTAVD), a technique developed by Vapor Technologies, Inc. of Mount Vernon, N.Y., to deposit metallic film on a polymeric substrate. The process involves striking an arc between electrodes in an evacuated space. At least one of the electrodes is made from the metallic material desired for deposition on the substrate. The arc causes vaporization and deposition of the electrode material on the substrate. Alternatively, metallic foils may be laminated between two polymeric films.

Figure 12B:
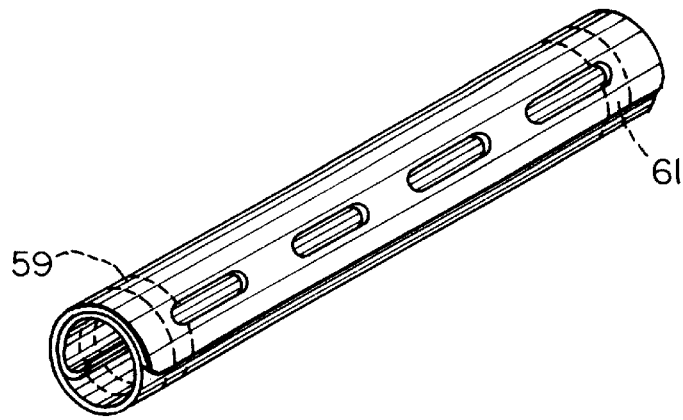
FIG. 12B is an illustration of the sheet of FIG. 12A rolled into a stent and in its low profile, relaxed configuration.
Figure 12C:
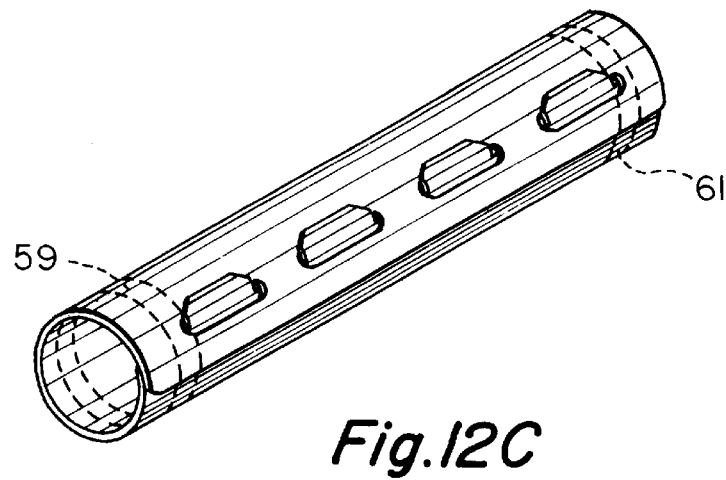
FIG. 12C is an illustration of the stent of 12B expanded and locked and illustrating the relative position of the radiopaque strips.
Figure 12A:
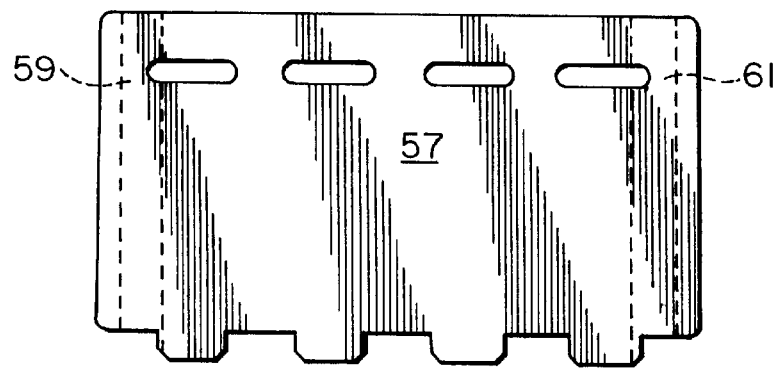
FIG. 12A is an illustration of a sheet similar to FIG. 11A but with the parallel strips extending along the direction substantially perpendicular to the axis about which the stent will be rolled.

FIGS. 12A–12C illustrate another embodiment of a stent having radiopaque indicia by which the location and configuration of the stent may be determined fluoroscopically. In this embodiment, the stripes 59, 61 are oriented perpendicular to the axis about which the sheet 57 will be rolled to the stent configuration. When in the low profile configuration illustrated in FIG. 12B, there will be a relatively large degree of overlapping of the stripes in a spiral configuration. The overlap presents a more radiopaque image than will be presented when the stent is in its expanded configuration (FIG. 12C) in which there will be less overlapping of the stripes, thereby presenting a less radiopaque image and an indication whether the deployment was successful.

Figure 13:
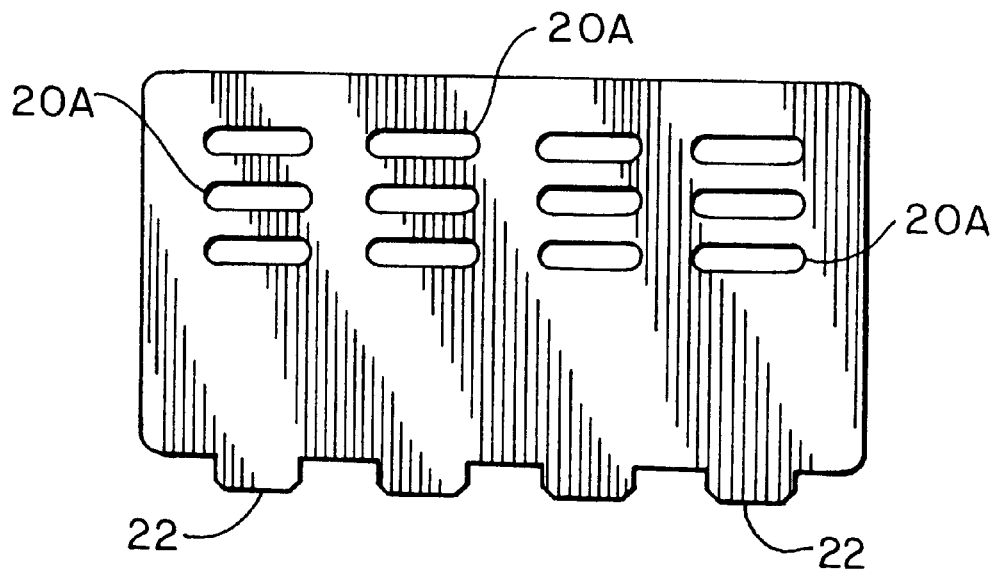
FIG. 13 is an illustration of an alternate embodiment of a sheet for forming a stent of the type shown in FIGS. 1–3 but in which the sheet is provided with a plurality of tab-receptive slots to enable the stent to be locked in one of a plurality of diameters.
Figure 14:
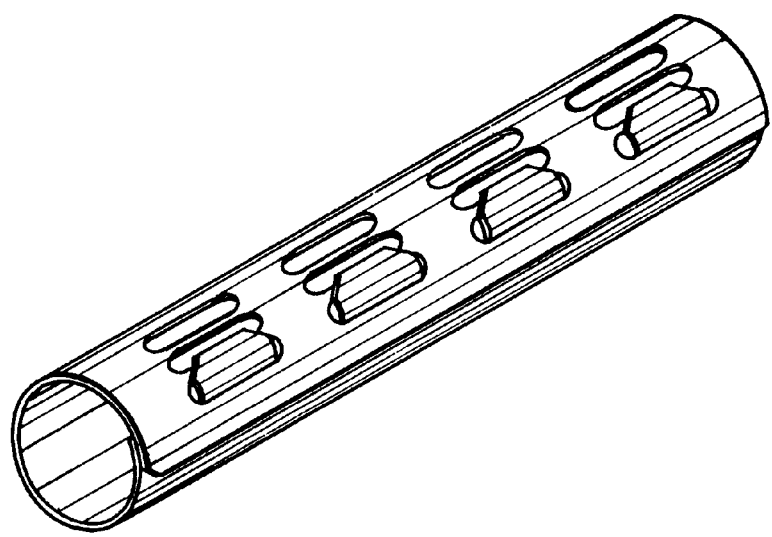
FIG. 14 is an illustration of the sheet of FIG. 13 rolled into a tubular stent configuration.

FIG. 13 illustrates a modification that may be made to any of the foregoing stents in order that the stent may be capable of being expanded and then locked selectively in one of a plurality of diameters. To this end, a plurality of circumferentially spaced slots 20A may be associated with each tab 22 on the sheet 12A. When the stent is expanded (FIG. 14) within the patient, the physician thus will be able to expand the device to two or more progressively increasing diameters. This is desirable because it may not always be possible to determine in advance precisely what the optimal stent diameter should be in a given case. By providing a plurality of slots 20A the physician can expand the device fully within the artery with increased assurance that the stent will be in firm engagement with the inner surface of the artery and will be locked securely in that configuration.

Figure 15:
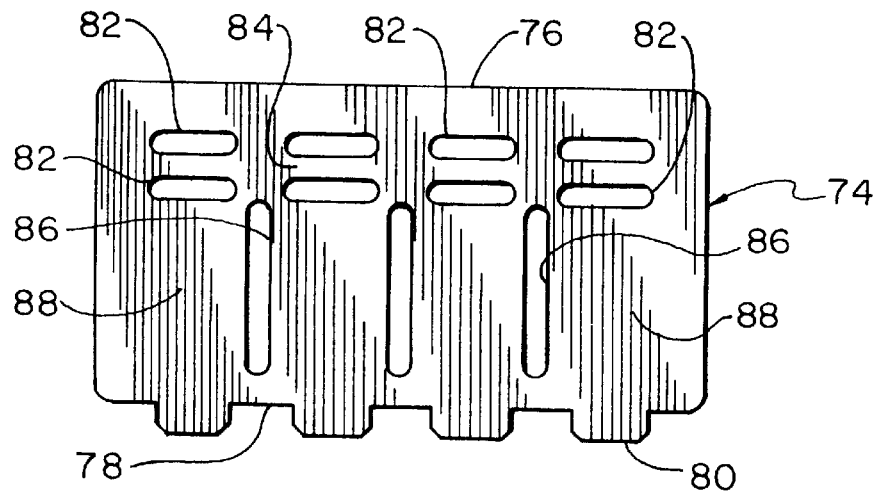
FIG. 15 is an illustration of a sheet of polymeric material for use in making a modified embodiment of the stent.
Figure 16:
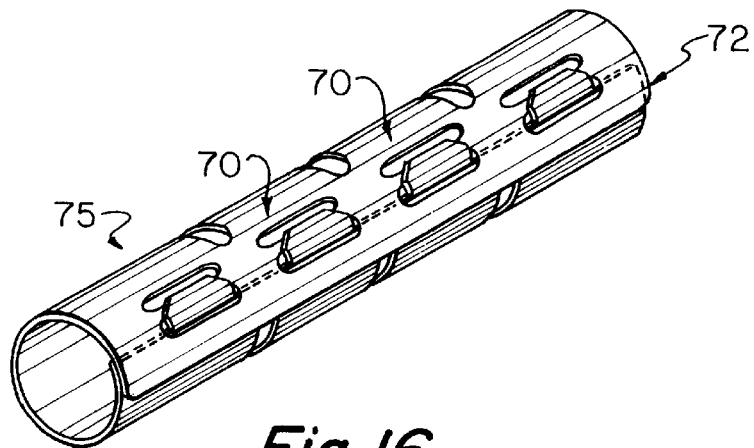
FIG. 16 and FIG. 16A are illustrations of the rolled-up stent formed from the sheet illustrated in FIG. 15 and showing the manner in which the sheet defines a plurality of longitudinally spaced hoops connected to each other by a substantially continuous but longitudinally flexible spine.
Figure 16A:
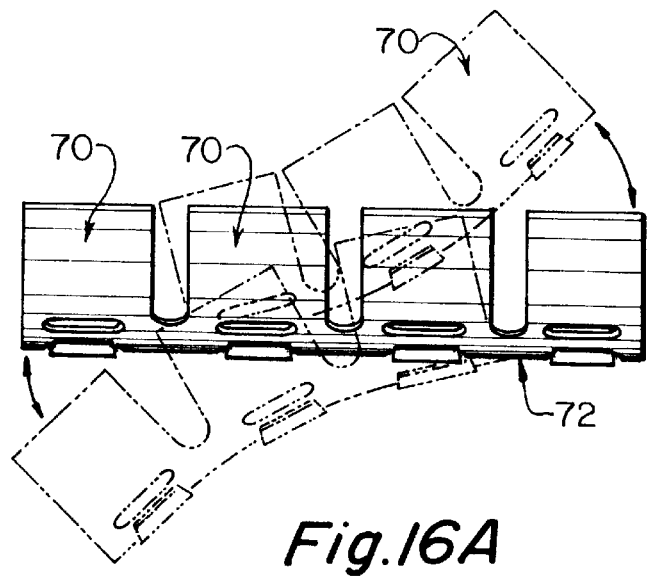

FIGS. 15 and 16 illustrate, respectively, a sheet 74 and a stent 75 formed from the sheet 74 in a further modified embodiment of the invention. As can be seen in FIG. 16, the stent 75 in this configuration includes a plurality of longitudinally spaced hoops 70 connected together by a longitudinally flexible spine 72. The hoops 70 provide the necessary hoop strength to prevent collapse of the stent under constricting force of the artery while the spine 72, being flexible (as suggested in phantom in FIG. 16A), maintains the desired longitudinal flexibility of the device when mounted on a balloon so that it can be navigated through tortuous arterial anatomy. The sheet 74 may be considered as including an outer longitudinal edge 76 and an inner longitudinal edge 78 on which tabs 80 are formed. Adjacent the outer longitudinal edge 76 and in alignment with each of the tabs 80 is at least one or more slots 82 adapted to receive the tabs 80. Each group of slots 82 is separated by a web 84. The slots are arranged to be in longitudinal alignment with each other as are the webs 84. The sheet 74 also includes a plurality of transverse slots 86 that define and separate intermediate segments 88 formable into hoops 70. The transverse slots 86 preferably extend from adjacent the inner longitudinal edge 78 to the region of the slots 82.

When the stent 75 is in its expanded configuration (FIG. 16), it will be appreciated that the hoop segments 88 define the hoops 70 and that the hoops 70 are unconnected except for the longitudinally extending, generally overlapping regions defined by the webs 84 and a margin 79 along the inner longitudinal edge 78. The continuous spine 72 thus defined, does not extend circumferentially to any appreciable extent and, therefore, is quite flexible thereby enabling the stent to have a high degree of longitudinal flexibility.

Figure 17:
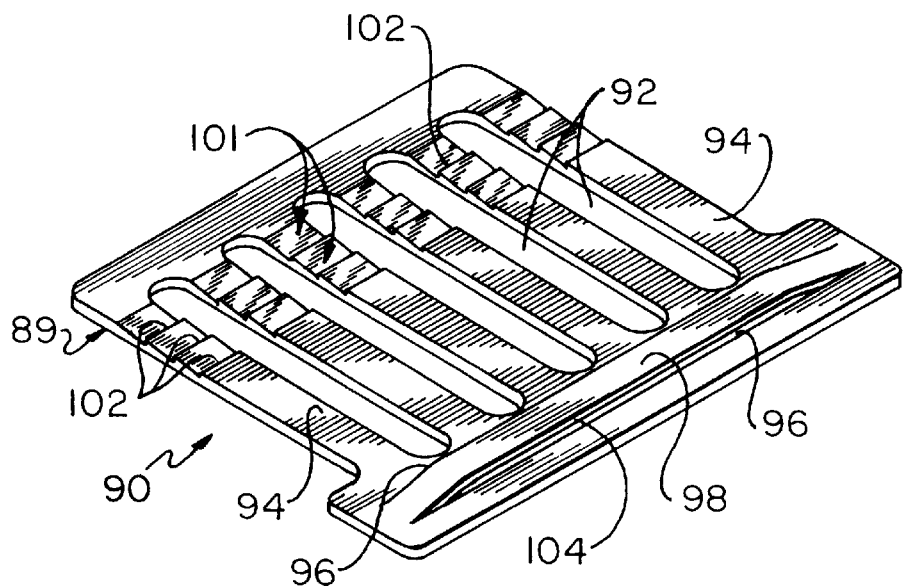
FIG. 17 is an illustration of a polymeric sheet for forming a modified embodiment of the stent.
Figure 18:
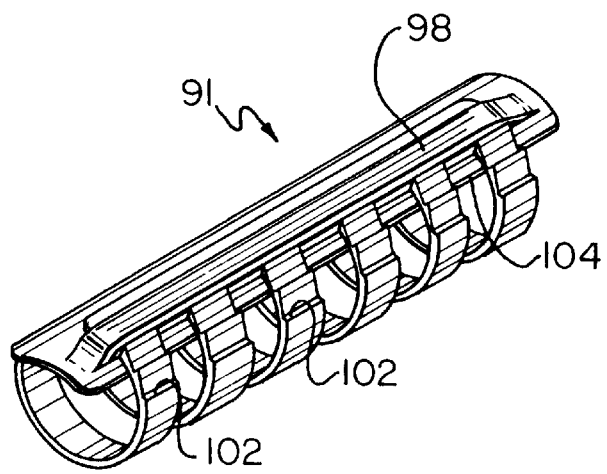
FIG. 18 is an illustration of a stent formed from the sheet shown in FIG. 17.

FIGS. 17 and 18 illustrate, respectively, a sheet 90 and a stent 91 formed from the rolled-up sheet 90 in accordance with another embodiment of the invention. In this embodiment one end of the stent defines a tongue-like member that is inserted through a slot on the opposite end of the sheet from which the stent is rolled and includes a locking mechanism that will lock the stent in one of the plurality of expanded configurations. In this embodiment the stent may be considered as "pre-locked" in that the tongue and slot are in engagement both in the low profile as well as in the expanded configuration. This assures that the tongue and slot will be in engagement at all times thereby further reducing the risk of non-engagement of the latching mechanism. In this embodiment, the sheet 90 may be die cut to include a plurality of transversely extending slots 92 that define, between the slots, a plurality of segments 94 that will form hoops when the sheet is rolled. One end of the sheet 90 is die cut with a pair of slits 96 that extend parallel to the intended longitudinal axis of the stent and define a longitudinally extending retention strip 98. The width of the sheet in the region in which the retention strip 98 is formed should be slightly greater than the remaining portion of the sheet so that the slits 96 are slightly longer than the width of the remaining portion of the sheet that contains the hoop segments 94. The outer surface of each of the hoop segments is formed to include one or more notches 101 configured to engage an edge 104 of the retention strap 98 as illustrated in FIG. 18. The notches 101 preferably are formed to include a surface 102 adapted to engage the retention strap edge 104 in full abutment to insure secure engagement of the notch with the retention strap edge. The notches 101 may be formed with any of a number of laser cutting devices that are commercially available.

Figure 18A:
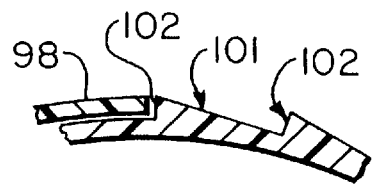
FIG. 18A is an enlarged illustration of the locking elements of the sheet as shown in FIG. 17.

When the sheet as shown in FIG. 17 is rolled into the stent configuration in FIG. 18, the free end of the sheet opposite the retention strap extends beneath the retention strap 98. After the stent is expanded by the balloon catheter, the notches 101 engage the edge 104 of the retention strap to lock the stent in its expanded configuration, the engagement of the notch 101 and edge 104 being illustrated in enlarged cross-sectional detail in FIG. 18A.

Figure 19:
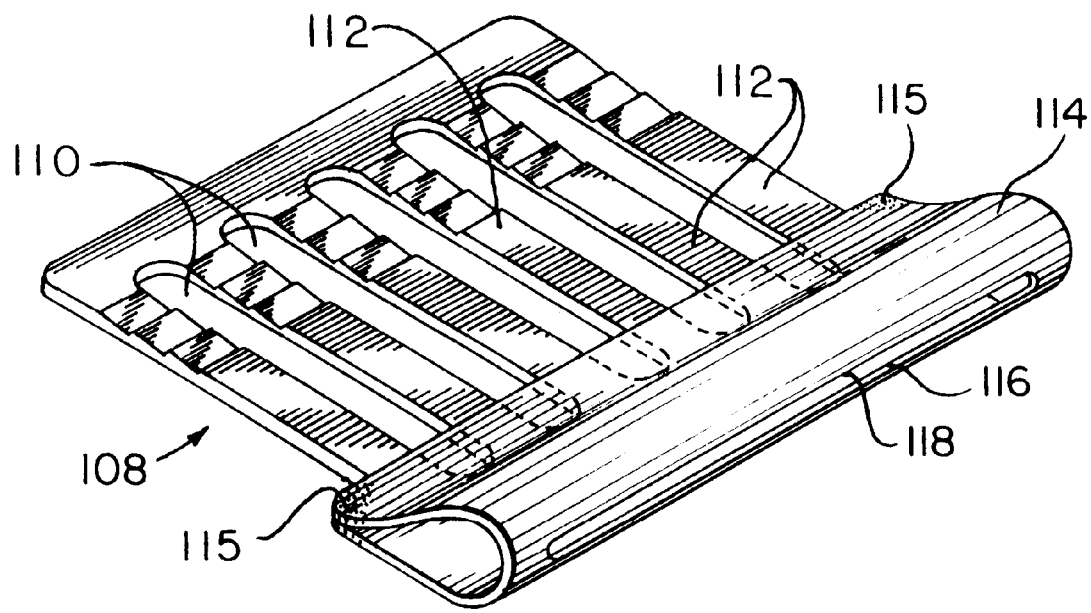
FIG. 19 is an illustration of a sheet of polymeric material folded and sealed in readiness to form another modified embodiment of the stent.
Figure 19A:
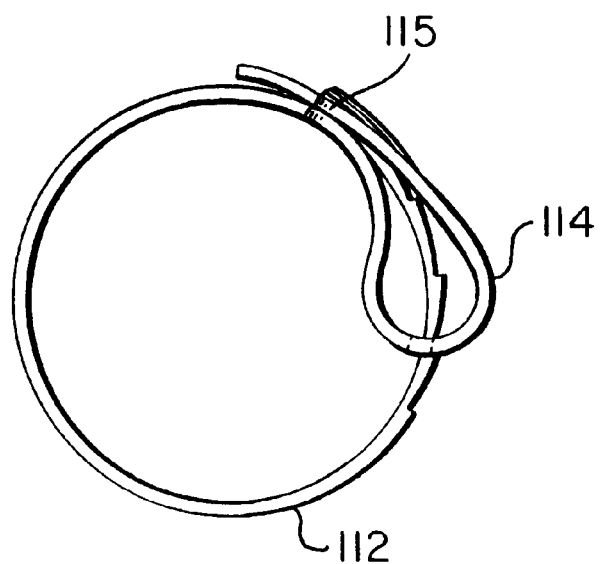
FIG. 19A is an enlarged illustration of the locking elements of the sheet as shown in FIG. 19.

FIG. 19 illustrates a partially formed modified embodiment of the stent shown in FIGS. 17 and 18. In this embodiment the sheet 108 also is formed with transverse slots 110 arranged to define hoop segments 112. A marginal portion 114 of the sheet is folded as shown in FIG. 19 and its corners 115 are attached, as by heat sealing or other suitable means, to the unfolded portion of the sheet, adjacent the ends of the slots 110. A longitudinally extending slot 116 is formed substantially along the folded-over portion. The slot 116 has a retention edge 118 and is slightly wider than the width of the other portions of the sheet. Thus, the portions of the sheet retaining the hoop segments 112 can be rolled into a tubular configuration (FIG. 19A) and the outer edge can be passed through the slot 116. As described above in connection with the embodiment of FIGS. 17 and 18, notches 101 are formed in the surfaces of the hoop segments that will engage the retention edge 118 so that the notches can become caught on the retention edge 118 thereby locking the device in an open configuration.

Figure 20:
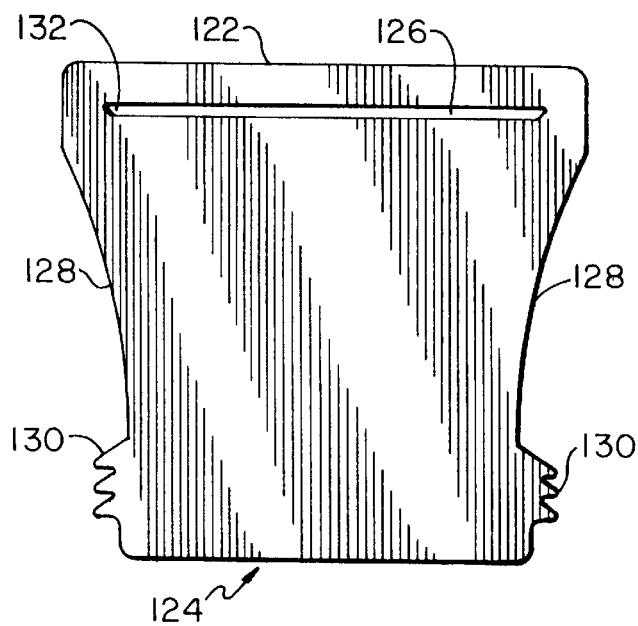
FIG. 20 is an illustration in plan of another embodiment of a die stamped polymeric sheet formable into another embodiment of the stent.
Figure 20A:
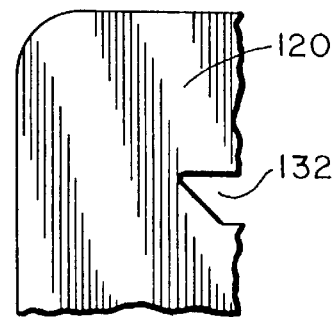
FIG. 20A is an enlarged illustration of one end of the slot in the sheet of FIG. 20.
Figure 21A:
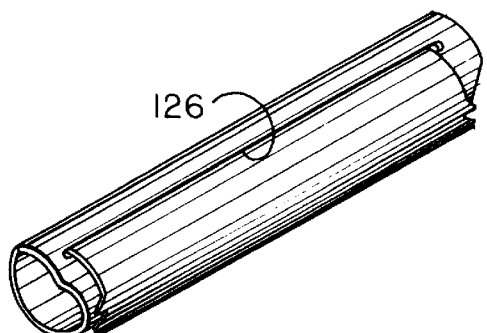
FIG. 21A is an illustration of the stent formed from the sheet of FIG. 20 in a low profile configuration.
Figure 21B:
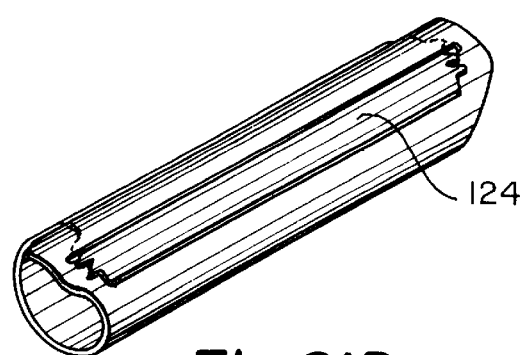
FIG. 21B is an illustration of the stent formed from the sheet of FIG. 20 and expanded and locked in its expanded configuration.

FIGS. 20 and 21 show, respectively, a die stampable sheet and a stent rolled from the sheet in accordance with another embodiment of the invention. This embodiment, as the embodiment as shown in FIGS. 18 and 19 also is pre-locked, that is, the tongue is in engagement with the slot when the stent is in its low profile configuration as well as when it is in its expanded configuration. As described above in connection with the embodiment of FIGS. 18 and 19, this assures that the locking mechanism will engage when the device is expanded. In this embodiment, the sheet 120 is formed to include a slot end 122 and a tongue end 124. The slot end is wider than the tongue end and includes a slot 126 that extends along the intended lengthwise dimension of the stent. The side edges 128 of the sheet 120 converge somewhat so that the tongue end 124 of the sheet is narrower than the length of the slot 126. When the sheet thus configured is in its rolled configuration, the tongue end 124 can pass through the slot 126, as shown in FIG. 21A.

Figure 20B:
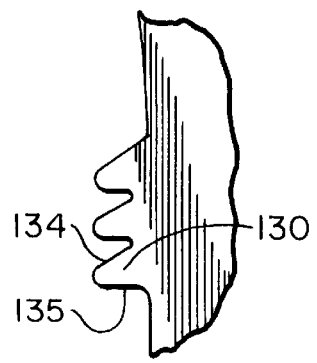
FIG. 20B is an enlarged illustration of the locking elements of the sheet as shown in FIG. 20.

In order to enable the stent to be locked in an open configuration, the side edges 128 of the sheet 120 near the tongue end 124 are provided with one or more teeth 130 dimensioned and configured to engage the ends 132 of the slot 126. In the low profile configuration, all of the teeth are disposed on the portion of the tongue that extends through and beyond the slot (FIG. 21A). Upon expansion of the stent (FIG. 21B) by the balloon catheter, the tongue is progressively withdrawn through the slot 126. As the teeth 130 engage the ends 132 of the slot, they will lock against the ends 132 of the slot to prevent return of the stent to its low profile configuration. As shown, a plurality of teeth 130 may be provided, thereby enabling the device to be expanded to one of several diameters. The teeth preferably are formed as shown in enlarged detail in FIG. 20B. Each of the teeth is provided with an angled edge 134 disposed at an angle to the extended lengthwise dimension of the stent and a parallel edge 135 that extends parallel to the intended lengthwise dimension of the stent. The angled edge 134 is disposed on the side of the teeth that face the slot end 122 of the sheet while the parallel edges 135 of the teeth 130 face the tongue end. The teeth are sufficiently flexible so that they can bend to permit the tongue to be withdrawn through the slot as the stent is expanded. Additionally, it is preferred that the ends of the slot 132 be formed at an angle, preferably of the order of about 45°, so that the slot may be considered as defining a long, flat trapezoidal configuration. The angled configuration of the ends of the slot enhance the locking engagement of the teeth with the ends of the slot. It should be understood that this embodiment of the invention, as the others, may be formed from multiple layer sheets such as suggested in FIGS. 7, 7A or to include radiopaque film, drug releasing layers, or other characteristics and combinations thereof.

Figure 22:
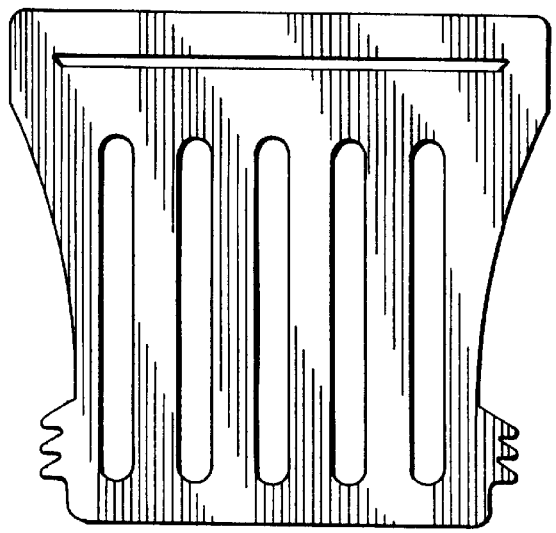
FIG. 22 is an illustration of a sheet formable into a stent and similar to the sheet of FIG. 20 modified to include cut-outs that serve to define a plurality of spaced hoops when the device is rolled into a stent configuration.
Figure 23A:
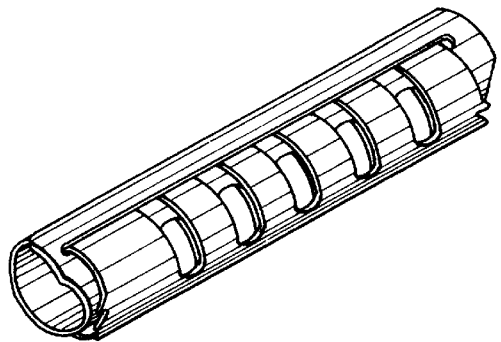
FIG. 23A is an illustration of a stent rolled from the sheet shown in FIG. 22 and in its low profile configuration.
Figure 23B:
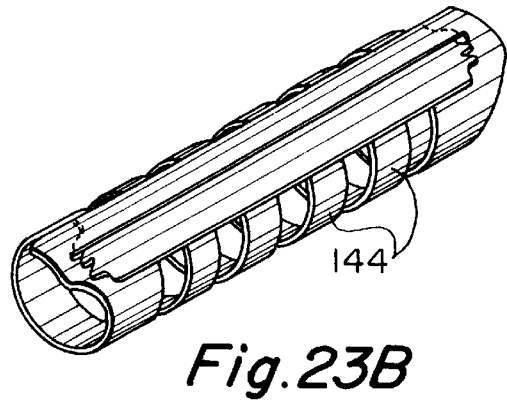
FIG. 23B is an illustration of the stent as shown in FIG. 23A in its expanded and locked configuration.

FIGS. 22 and 23A and 23B illustrate, respectively, a modified embodiment of a sheet and a stent formed from that sheet in accordance with the invention. This embodiment is similar to that described above and illustrated in FIGS. 20 and 21 but modified to include a plurality of circumferentially extending longitudinally spaced slots that define hoop segments therebetween. The hoop segments form hoops 144 substantially in the manner described above in connection with the embodiment illustrated in FIGS. 15 and 16. The uninterrupted portions of the sheet defined at the tongue end and at the slot end cooperate to define a longitudinally extending flexible spine by which the stent may have a high degree of longitudinal flexibility while maintaining substantial hoop strength. This embodiment presently is considered to be the preferred embodiment.

Figure 24:
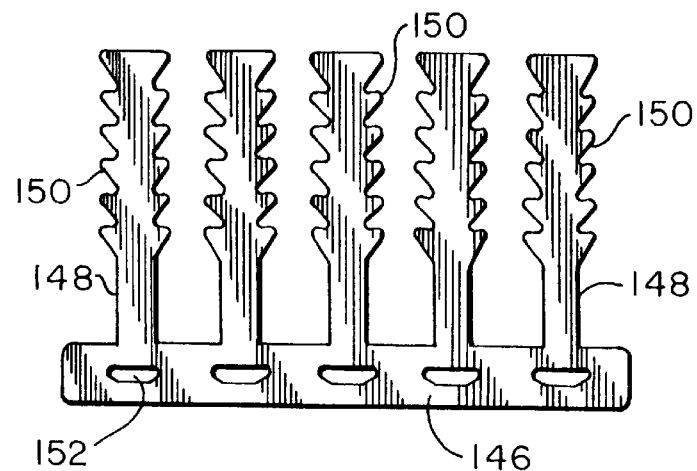
FIG. 24 is a plan illustration of a die-cut sheet to form another embodiment of the invention.
Figure 25:
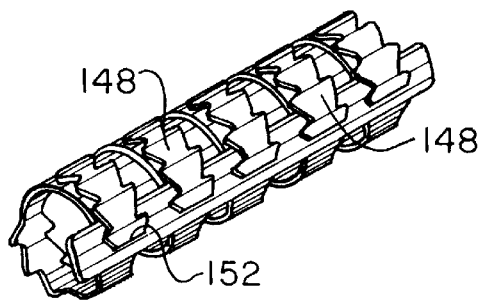
FIG. 25 is an illustration of a stent rolled from the sheet illustrated in FIG. 24 in its low profile configuration in readiness to be expanded.
Figure 26:
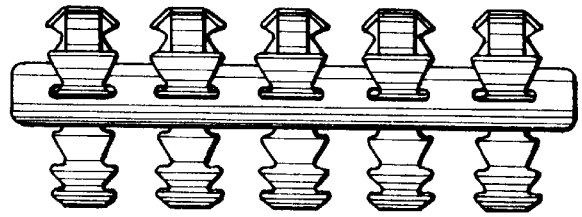
FIG. 26 is an illustration of the stent of FIG. 25 in an expanded configuration.

FIGS. 24 and 25 illustrate a further embodiment of a die stampable sheet and stent formed from the sheet, respectively, in accordance with the invention. In this embodiment, the sheet is formed to define a longitudinally extending base strip 146 having a plurality of transversely extending longitudinally spaced locking strips 148 integral with the base strip 146. Each of the locking strips is provided with a plurality of teeth 150 along its edges. A longitudinally extending slot 152 is formed in the base strip 146 in association with each of the locking strips. FIG. 25 illustrates the device in its rolled form. Each of the locking strips 148 is passed through its associated slot 152 with the portion of the locking strips 148 extending exteriorly of the stent and lying closely to the exterior of the stent. The teeth are configured to engage the ends of each of the slots so as to permit withdrawing of the locking strips 148 through the slots when the stent is expanded but to lock and resist movement in the opposite direction. Thus, when the stent is expanded to the desired extent, it will resist return to low profile configuration. In this embodiment, as in the previously described embodiment, the stent defines a configuration of a plurality of hoops defined by the locking strips and connected to each other along a longitudinally extending flexible spine thereby to provide substantial hoop strength combined with high longitudinal flexibility.

Figure 27:
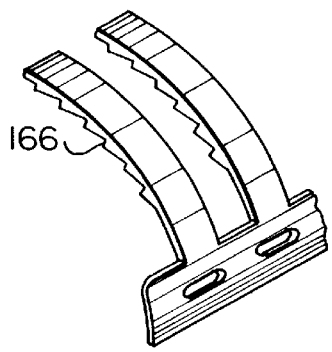
FIG. 27 is an illustration of a modified lock for the stent shown in FIGS. 24–26.
Figure 28:
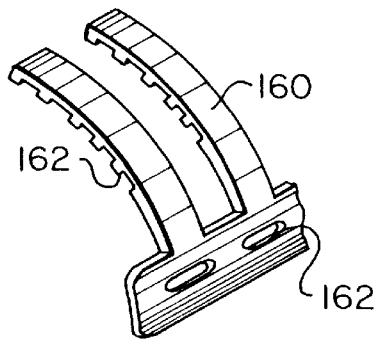
FIG. 28 is an illustration of another modified locking element that may be used in connection with the stent shown in FIGS. 24–26.

FIG. 28 illustrates a device similar to that described in FIGS. 24 and 25 modified in its locking mechanism. In the embodiment shown in FIG. 28, the transverse strips 160 are provided with a plurality of slots 162 cut into a surface of the strip, the slots being cut to engage a retention edge of the slots 152. In the embodiment shown in FIG. 27, the device is compression molded rather than stamped from a sheet and is provided with a plurality of projecting teeth 166.

It should be understood that the foregoing description of the invention is intended merely to be illustrative thereof and that other embodiments, modifications and equivalents may be apparent to those skilled in the art without departing from its spirit.

Having thus described the invention what we desire to claim and secure by Letters Patent is:

1. A percutaneously placeable stent comprising:
    a sheet of substantially uniform thickness rolled into a tubular shape and being expandable from a relatively small diameter low profile configuration to an expanded configuration of greater diameter, the sheet having at least one slot and at least one locking strip extending through the slot when the stent is in its low profile state, the locking strip and slot being configured to lock and prevent contraction of the tube to a smaller diameter when the diameter of the stent is expanded, the strip being arranged to be drawn through the slot as the stent diameter is expanded.

2. A stent as claimed in claim 1 having a pair of said slots defining a longitudinal retention strip extending along one end of the sheet under which the opposite end of the sheet passes.

3. A stent as claimed in claim 1 having a single slot defining a retention edge on one end of the sheet, the locking strip extending through the slot and being engageable with the retention edge.

4. A stent as claimed in claim 1 wherein said locking elements are teeth located on the side of the locking strip for engaging the edges of the slot.

5. A stent as claimed in claim 1 wherein said locking elements are molded in tabs.

6. A stent as claimed in claim 1 wherein said locking elements are laser cut grooves.

7. A stent as claimed in claim 1 wherein the sheet further comprises slots extending perpendicular to the lengthwise dimension of the rolled stent.

8. A stent as claimed in claims 1 or 7 wherein the sheet is formed so that the stent comprises a plurality of said locking strips connected to and extending transversely of a longitudinal strip, the locking strips and longitudinal strip being arranged to define a plurality of spaced hoops connected by a spine for providing longitudinal flexibility and hoop strength to the stent.

9. A stent as claimed in claim 1 wherein the sheet is polymeric.

10. A stent as claimed in claim 1 wherein the sheet is bioabsorbable.

11. A stent as claimed in claim 1 wherein the sheet is multilayered.

12. A stent as claimed in claim 1 wherein the sheet has radiopaque indicia arranged to provide both the location and configuration of the stent in vivo.

13. A stent as claimed in claim 1 wherein the sheet includes a plurality of transverse locking strips for extending through a plurality of longitudinal slots located on a longitudinal base strip of the sheet.

14. A stent as claimed in claim 13 wherein the locking strips further comprise locking elements.

15. A stent as claimed in claim 14 wherein the locking elements are in the form of teeth located on the sides of the locking strips for engaging the edges of a slot.

16. A stent as claimed in claim 14 wherein the locking elements are molded in tabs located on a radially inwardly facing surface.

17. A stent as claimed in claim 14 wherein the locking elements are laser cut grooves located on a radially inwardly facing surface.

18. A stent as claimed in claim 13 wherein the sheet is polymeric.

19. A stent as claimed in claim 13 wherein the sheet is bioabsorbable.

20. A stent as claimed in claim 13 wherein the sheet is multilayered.

21. A stent as claimed in claim 13 wherein the sheet includes radiopaque indicia arranged to indicate both the location and configuration of the stent in vivo.

22. A stent as claimed in claim 21 wherein the radiopaque indicia is laminated into the sheet.

23. A stent as claimed in claim 21 wherein the radiopaque indicia is supplied and attached to the sheet by vapor deposition.

24. A stent and delivery catheter continuation comprising:
   a stent as defined in any one of the claims 1 or 21;
   a catheter having proximal and distal ends and having a balloon at its distal end, means for inflating and deflating the balloon and means for engaging at least one end of the stent when the stent is mounted on the balloon, thereby to retain the stent on the balloon during percutaneous delivery of the device;
   the stent retaining means being constructed and arranged to release the stent system expansion of the balloon and the stent.

25. A stent as claimed in claim 1 wherein the locking strips further comprise locking elements.

* * * * *